(12) United States Patent
Thor

(10) Patent No.: US 7,718,705 B1
(45) Date of Patent: May 18, 2010

(54) METHODS OF USING RAPID-ONSET SELECTIVE SEROTONIN REUPTAKE INHIBITORS FOR TREATING SEXUAL DYSFUNCTION

(75) Inventor: Karl Bruce Thor, Morrisville, NC (US)

(73) Assignee: Eli Lilly and Company, Indianapolis, IN (US)

( * ) Notice: Subject to any disclaimer, the term of this patent is extended or adjusted under 35 U.S.C. 154(b) by 869 days.

(21) Appl. No.: 10/049,427

(22) PCT Filed: Aug. 22, 2000

(86) PCT No.: PCT/US00/20788

§ 371 (c)(1),
(2), (4) Date: May 6, 2002

(87) PCT Pub. No.: WO01/17521

PCT Pub. Date: Mar. 15, 2001

(51) Int. Cl.
*A01N 33/02* (2006.01)
*A61K 31/135* (2006.01)
*A61K 31/13* (2006.01)

(52) U.S. Cl. ....................... 514/651; 514/641
(58) Field of Classification Search ................. 514/651, 514/641
See application file for complete search history.

(56) References Cited

U.S. PATENT DOCUMENTS

| | | | |
|---|---|---|---|
| 4,940,731 A | 7/1990 | Bick | |
| 5,114,976 A | 5/1992 | Norden | |
| 5,135,947 A * | 8/1992 | Robertson et al. | 514/466 |
| 5,151,448 A | 9/1992 | Crenshaw et al. | |
| 5,248,699 A | 9/1993 | Sysko et al. | |
| 5,276,042 A | 1/1994 | Crenshaw et al. | |
| 5,283,263 A | 2/1994 | Norden | |
| 5,457,121 A | 10/1995 | Schaus et al. | |
| 5,552,429 A | 9/1996 | Wong et al. | |
| 5,576,321 A | 11/1996 | Krtushinski, Jr. et al. | |
| 5,589,511 A | 12/1996 | Young et al. | |
| 5,589,512 A | 12/1996 | Norden | |
| 5,597,826 A | 1/1997 | Howard et al. | |
| 5,614,523 A | 3/1997 | Audia et al. | |
| 5,627,196 A | 5/1997 | Audia et al. | |
| 5,672,612 A | 9/1997 | Rosen et al. | |
| 5,707,999 A | 1/1998 | Cavallini | |
| 5,744,501 A | 4/1998 | Norden | |
| 5,789,402 A | 8/1998 | Audia et al. | |
| 5,789,449 A | 8/1998 | Norden | |
| 5,830,500 A | 11/1998 | El-Rashidy et al. | |
| 5,846,982 A | 12/1998 | Audia et al. | |
| 5,897,864 A | 4/1999 | Cohen | |
| 5,910,319 A | 6/1999 | Anderson et al. | |
| 5,912,256 A | 6/1999 | Koch et al. | |
| 5,922,341 A | 7/1999 | Smith et al. | |
| 6,037,360 A | 3/2000 | Smith et al. | |
| 6,046,215 A | 4/2000 | Audia et al. | |
| 6,107,307 A | 8/2000 | Audia et al. | |
| 6,228,864 B1 | 5/2001 | Smith et al. | |
| 6,303,627 B1 | 10/2001 | Koch et al. | |
| 6,517,866 B1 | 2/2003 | Am Ende et al. | |
| 6,525,048 B1 | 2/2003 | Bright | |

FOREIGN PATENT DOCUMENTS

| | | |
|---|---|---|
| EP | 714663 A2 | 6/1996 |
| EP | 924205 B1 | 6/1999 |
| WO | WO 96/12485 | 5/1996 |
| WO | WO 96/24353 | 8/1996 |
| WO | WO 97/13770 | 4/1997 |
| WO | WO 97/47302 | 12/1997 |
| WO | 99/01132 | 1/1999 |
| WO | WO 99/01113 | 1/1999 |
| WO | WO 99/01122 | 1/1999 |
| WO | WO 99/01132 | 1/1999 |
| WO | WO 99/16440 | 4/1999 |
| WO | WO 99/21508 | 5/1999 |
| WO | WO 99/65487 | 12/1999 |
| WO | WO 00/06160 | 2/2000 |
| WO | WO 00/07994 | 2/2000 |
| WO | WO 00/21521 | 4/2000 |
| WO | WO 00/67729 | 11/2000 |
| ZA | 9 300 694 | 6/1993 |

OTHER PUBLICATIONS

Livini et al, 121CA:128898, 1994.*
Lee et al, 128CA:10222, 1996.*
Lane, R.M., 127CA:287476, 1997.*
Houck, Carl, 129CA:156848, 1998.*
Baldwin et al, 126CA:180636, 1995.*
CG McMahon, Et Al: "Treatment of Premature Ejaculation with Paroxetine Hydrochloride" International Journal of Impotence Research (1999)11, 241-246.
Genupro subsidiary has dapoxetine in Phase II trials for premature ejaculation . . . The Pink Sheet, Apr. 26, 1999.

(Continued)

*Primary Examiner*—Yong S Chong
(74) *Attorney, Agent, or Firm*—Sheridan Ross P.C.

(57) ABSTRACT

Methods for the prevention, treatment, or management of sexual dysfunction, such as premature ejaculation, by administering to a patient in need of therapy a therapeutically effective amount of a rapid-onset selective serotonin reuptake inhibitor on an as-needed basis shortly before sexual activity.

10 Claims, 2 Drawing Sheets

OTHER PUBLICATIONS

Self therapy with sertraline given prn at 5 pm in treatment of premature ejaculation. Paick, J. et al., Journal of Urology, 159 (5 Supp.), p. 241, May 1998.

Sertraline hydrochloride for premature ejaculation: Dosing schedule. Swartz, D. et al., Journal of Urology, 157 (4Supp.), p. 182, Apr. 1997.

Paroxetine as needed for premature ejaculation—Editorial Comment. Benson, G., Journal of Urology, vol. 61, No. 6, p. 1830, Jun. 1999.

Clomipramine versus placebo in the treatment of premature ejaculation: a pilot study. Segraves, R. et al., Journal of Sex and Martial Therapy, vol. 19, No. 3, pp. 198-200, Fall 1993.

Clomipramine in the treatment of rapid (premature) ejaculation. Strassberg, D. et al., Journal of Sex and Marital Therapy, 25(2), pp. 89-101, Apr.-Jun. 1993.

Fluoxetine and premature ejaculation: A double-bline, crossover, placebo-controled study. Haensel, S. et al., Journal of Clinical Psychopharmacology, vol. 18, No. 1, pp. 85-94, Mar. 1995.

Pharmacologic treatment of rapid ejaculation, Althof, S., Clinical Sexuality, vol. 18, No. 1, pp. 85-94, Mar. 1995.

Clormipramine and sexual function in men with premature ejaculation, Haensel, S. et al., Journal of Urology, 156(4), pp. 1310-1315, Oct. 1996.

Treatment of premature ejaculation with Lorazepam, Seagraves, R. American Journal of Psychiatry, 144:9, p. 1240 Sep. 1987.

Hamilton et al., "Determination of dapoxetine, an investigational agent with the potential for treating depression, and its mono- and di-desmethyl metabolites in human plasma using column-switching high-performance liquid chromatography," *Journal of Chromatography* 1993, 612:253-261.

Waldinger et al., "Antidepressants and ejaculation: a double-blind, randomized, fixed-dose study with mirtazapine and paroxetine," *J. Clin. Psychopharmacology* 2003, 23(5):467-470, Abstract only, from PubMed—PMID:14520123.

Kennedy et al., "Antidepressant-induced sexual dysfunction during treatment with moclobemide, paroxetine, sertraline, and venlafaxine," *J. Clin Psychiatry* 2000, 61(4):276-281, Abstract only, from PubMed—PMID:10830148.

McMahon, C., J. Sex Med., Supp2:94-5 (2005).

Day, SJ and Altman, DG Blinding in Clinical Trials and Other Studies, *British Medical Journal*, 321:504 (2000).

Swartz, D.A. (1994), Sertraline hydrochloride for premature ejaculation. J Urol 151 (*Suppl.*); 345A.

M.H. Beers and R. Berkow: "The Merk Manual of Diagnosis and Therapy, Seventeenth Edition" (Jan. 1999), XP002157328, p. 1558.

McMahon Chris G. Et Al: "Treatment of Premature Ejaculation with Paroxetine Hydrochloride as needed: 2 Single-Blind Placebo Controlled Crossover Studies." Journal of Urology, vol. 161, No. 6, (Jun. 1999) pp. 1826-1830) XP00980381 ISSN: 002-5947.

McMahon Chris G. "Treatment of Premature Ejaculation with Sertraline Hydrochloride: A Single-Blind Placebo Controlled Crossover Study." Journal of Urology, vol. 159, pp. 1935-1938.

CG McMahon: "Treatment of Premature Ejaculation with Sertraline Hydrochloride" International Journal of Impotence Research (1998) 10, 181-184.

CG McMahon, Et Al: Treatment of Premature Ejaculation with Paroxetine Hydrochloride As needed: 2 Single-Blind Placebo Controlled Crossover Studies Journal of Urology, vol. 161(6), Jun. 1999, pp. 1826-1830.

Parsley Power-Smith: "Beneficial Sexual Side-Effects from Fluoxetine": British Journal of Psychiatry (1994), 164, 249-250.

Marcel D. Waldinger, M.D., Et Al: "Paroxetine Treatment of Premature Ejaculation: A Double-Blind, Randomized, Placebo-Controlled Study" (Am J Psychiatry 1994; 151:1377-1379).

M.D. Waldinger, Et Al: "Ejaculation-Retarding Properties of Paroxetine in Patients with Primary Premature Ejaculation: A Double-Blind, Randomized, Dose-Response Study" British Journal of Urology (1997), 79, 592-595.

M.D. Waldinger, Et Al: "Selective Serotonin Reuptake Inhibitor-Induced Sexual Dysfunction: Clinical and Research Considerations" International Clinical Psychopharmacology 1998, vol. 13 (suppl 6) S27-S33.

Marcel D. Waldinger, MD, PhD, Et Al: Effect of SSRI Antidepressants on Ejaculation: A Double-Blind, Randomized, Placebo-Controlled Study with Flouxetine, Fluvoxamine, Paroxetine, and Sertraline: Journal of Clinical Psychopharmacology, vol. 18, No. 4, (1998) p. 274-281.

Stanley E. Elthof, PhD. "Pharmacologic Treatment of Rapid Ejaculation"The Psychiatric Clinics of North America vol. 18, No. 1, Mar. 1995, p. 85.

Joseph Mendels, MD, Et Al: "Sertraline Treatment for Premature Ejaculation" Journal of Clinical Psycopharmacology, vol. 15, No. 5, p. 341, 1995.

G.M. Ludovico, Et Al: "Paroxetine in the Treatment of Premature Ejaculation" British Journal of Urology (1998) 77, 881-882.

Hayrettin Kara, Et Al: "The Efficacy of Fluoxetine in the Treatment of Premature Ejaculation: A Double-Blind Placebo Controlled Study" The Journal of Urology, vol. 156, 1631-1632, Nov. 1996.

Richard Balon, "Antidepressants in the Treatment of Premature Ejaculation" Journal of Sex & Marital Therapy, vol. 22, No. 2, 1996, p. 85.

Hong Shick Lee, MD, PhD, Et Al: "An Open Clinical Trial of Fluoxetine in the Treatment of Premature Ejaculation" Journal of Clinical Psychopharmacology, vol. 16, No. 5, p. 379, 1996.

R.M. Lane "A Critical Review of Selective Serotonin Reuptake Inhibitor-Related Sexual Dysfunction; Incidence, Possible Aetiology and Implications for Management" Journal of Psychopharmacology 11(1) (1997) 72-82.

S. Kindler, Et Al: "The Treatment of Comorbid Premature Ejaculation and Panic Disorder with Fluoxetine" Clinical Neuropharmacology, vol. 20, No. 5. pp. 466-471.

Angel L. Montejo-Gonzalez, Et Al: "SSRI-Induced Sexual Dysfunction: Fluoxetine, Paroxetine, Sertraline, and Fluvoxamine in a Prospective, Multicenter, and Descriptive Clinical Study of 344 Patients" Journal of Sex & Marital Therapy, vol. 23, No. 3, Fall 1997, p. 176.

Sae Chul Kim, Et Al: "Efficacy and Safety of Fluoxetine, Sertraline and Clomipramine in Patients with Premature Ejaculation: A Double-Blind, Placebo Controlled Study" The Journal of Urology, vol. 159, 425-427, Feb. 1998.

J.T. Hsieh, Et Al: In vivo Evaluation of Serotonergic Agents and α-adrenergic Blockers on Premature Ejaculation by Inhibiting the Seminal Vesicle Pressure Response to Electrical Nerve Stimulation, British Journal of Urology (1998), 82, 237-240.

B. Olivier, Et Al: "Setotonin, Serotonergic Receptors, Selective Serotonin Reuptake Inhibitors and Sexual Behaviour" International Clinical Psychopharmacology 1998, vol. 13 (suppl 6):S9-S14.

McMahon Chris G. Et Al: "Treatment of Premature Ejaculation with Paroxetine Hydrochloride as needed: 2 Single-Blind Placebo Controlled Crossover Studies." Clinical of Urology, vol. 161, No. 6, (Jun. 1999) pp. 1826-1830).

H. Biri, Et Al: "Sertraline in the Treatment of Premature Ejaculation: A Double-Blind Placebo Controlled Study" International Urology and Nephrology 30 (5), pp. 611-615 (1998).

Ugur Yilmaz, Et Al: "The Effects of Fluoxetine on Several Neurophysiological Variables in Patients with Premature Ejaculation" The Journal of Urology, vol. 161, 107-111, Jan. 1999.

Rosen, Raymond C. PhD, Et Al: "Effects of SSRIs on Sexual Function: A Critical Review" Journal of Clinical Psychopharmacology, vol. 19(1), Feb. 1999; pp. 67-85.

Jan Mos, Et Al: "A Comparison of the Effects of Different Serotonin Reuptake Blockers on Sexual Behavior of the Male Rat" European Neuropsychopharmacology 9 (1999) 123-135.

Willem Meinhardt, Et Al: Comparative Tolerability and Efficacy of Treatments of Impotence, Drug Safety Feb. 1999 20(2) 133-146.

P.G. Cohen, Et Al: "Effects of Fenfluramine on Ejaculatory Function, Luteinizing Hormone and Testosterone Levels in Men with Hypogonadotropic Hypogonadism and Premature Ejaculation" International Clinical Psychopharmacology 1999, vol. 14, No. 2, pp. 91-94.

Soo Woong Kim, Et Al: "Short-Term Analysis of the Effects of as Needed use of Sertraline at 5 PM for the Treatment of Premature Ejaculation" Urology 54 (3) 1999, p. 544-547.

M. Murat Basar, Et Al: Comparison of Sertraline to Fluoxetine with Regard to Their Efficacy and Side Effects in the Treatment of Premature Ejaculation: Arch. Esq. De Urol., 52.9 (1,008-1,011), 1999.

Thomas N. Wise, M.D.: "Sertraline as a Treatment for Premature Ejaculation" Journal of Clinical Psychiatry 55:9, Sep. 1994, p. 417.

Peter Forster, M.D., Et Al: "Fluoxetine for Premature Ejaculation" American Journal Psychiatry 141:10, Oct. 1994, p. 1523.

B. Giammunno, Et Al: "LaParoxetina Nel Trattamento Dell'Eiaculazione Precoce", Arch. It. Urol., LXIX: 11-13, 1997.e Per M. Isaksen: "The Effect of an Anti-depressive Drug on Premature Ejaculation" Tidsskr Nor Laegeforen nr. 13, 1995; 115, p. 1616-7.

Paick JS, et al: "Self therapy with sertraline given PRN at 5 pm in treatment of premature ejaculation" Journal of Urology 241, (May 1998), vol. 159, No. 5, Supplement XP00980386.

CG McMahon, Et Al: "Treatment of Premature Ejaculation with Paroxetine Hydrochloride" International Journal of Impotence Research (1999)11, 241-246.

Yells et al., Pharmacology Biochemistry and Behavior, vol. 49, No. 1, pp. 121-127 (1994).

* cited by examiner

METHODS OF USING RAPID-ONSET SELECTIVE SEROTONIN REUPTAKE INHIBITORS FOR TREATING SEXUAL DYSFUNCTION

This application is a national stage application under 35 U.S.C. 371 of PCT Application No. PCT/US00/20788 having an international filing date of Aug. 22, 2000, which designated the United States, which PCT application claimed the benefit of U.S. Provisional Application No. 60/152,435, filed Sep. 3, 1999.

The invention relates to methods for the prevention, treatment, or management of sexual dysfunction in mammals, particularly premature ejaculation in men, by administering a therapeutically effective amount of a rapid-onset selective serotonin reuptake inhibitor, or a pharmaceutically acceptable salt thereof, on an as-needed basis shortly before sexual activity.

A normal erection occurs as a result of a coordinated vascular event in the penis, which is usually triggered neurally and includes vasodilation and smooth muscle relaxation in the penis and its supplying arterial vessels. Arterial inflow causes enlargement of the substance of the corpora cavernosa. Venous outflow is trapped by this enlargement, permitting sustained high blood pressures in the penis normally sufficient to cause rigidity. Muscles in the perineum also assist in creating and maintaining penile rigidity. Erection may also be induced centrally in the nervous system by sexual thoughts or fantasy, and is usually reinforced locally by reflex mechanisms. Erectile mechanics in women are substantially similar for the clitoris. In men, however, ejaculation typically occurs with an orgasm.

Premature ejaculation, however, is one of the most common sexual complaints. It is estimated to affect up to 30 to 40 percent of men, i.e., approximately 36 million American men (Derogatis, L. R., *Med. Aspects Hum. Sexuality*, 14:1168-76 (1980); Frank E., et al., *Engl. J. Med.*, 299:111-115 (1978); Schein, M., et al., *Fam. Pract. Res. J.*, 7(3):122-134 (1988)). Premature ejaculation means persistent or recurrent ejaculation with minimal sexual stimulation before, upon, or shortly after penetration, and before the person wishes it. Such ejaculation that occurs sooner than desired is often disappointing and can lead to other sexual dysfunctions including erectile difficulties, female inorgasmia, low sexual desire, and sexual aversion (Rust J., et al., *Br. J. Psychiat.*, 152:629-631 (1988)). Behavioral therapy, such as the Semans pause maneuver, the Masters and Johnson pause-squeeze technique or the Kaplan stop-start method, is considered the gold standard for the treatment of premature ejaculation (Seftel, A. D., Altohob, S. E., "Premature Ejaculation", *Diagnosis and Management of Male Sexual Dysfunction*, Edited by J. J. Mulcahy, New York, N.Y., Igaku-Shoin, (1997) Chapter 11, pages 196-203). While these techniques are harmless, usually painless, and are successful at rates of 60 to 95% (Seftel; Hawton, K., et al., *Behav. Res. Ther.*, 24:377 (1986)), they require partner cooperation and improvement is short-lived (Bancroft, J. and Coles, L., *Brit. Med. J.*, 1:1575 (1976) and De Amicus, L. A., et al., *Arch. Sex. Behav.*, 14:467 (1985)).

Premature ejaculation rarely has a physical cause, however, prostate gland inflammation or nervous system disorders may be involved. Treatment may involve certain selective serotonin reuptake inhibitors, such as fluoxetine, paroxetine, or sertraline (*Merck Manual of Medical Information* at 421-422, Home Edition, Merck Research Laboratories (1997)); see also U.S. Pat. Nos. 5,597,826 (sertraline), 5,276,042 (paroxetine), and 5,151,448 (fluoxetine). Although ejaculation latency is affected by psychological and/or cognitive mechanisms, somatic factors are also involved (Althof, S. E., *Psychiatr. Clin. N. Amer.*, 18(1):85-94 (1995); Rowland, D. L., et al., *J. Sex. Marital. Ther.*, 19:189 (1993)). Ejaculation is mediated partly through a neural reflex stimulated by sensory input to the penis, and terminating in smooth and striated muscle contractions that produce seminal emission and expulsion. Segraves hypothesized that increased serotoninergic activation may be associated with orgasmic inhibition (*Arch. Gen. Psychiatry.*, 46:275-284 (1989)) and reports that ejaculation seems to be mediated by $alpha_1$-receptor activation, presumably at a peripheral level with cholinergic fibers playing a modulatory role. Serotoninergic system involvement in ejaculation could occur at the level of the brain or spinal cord.

Several psychiatric drugs have been reported to have side effects of inhibiting ejaculation. Thus, oral pharmacotherapy for premature ejaculation using tricyclic antidepressants or certain selective serotonin re-uptake inhibitor drugs has been studied as an alternative to behavioral therapy (See, e.g., *Merck Manual of Medical Information* at 421-422, Home Edition, Merck Research Laboratories (1997)). Open-label and controlled studies have reported that these compounds increase intravaginal ejaculatory latency effectively while avoiding side effects in subjects with premature ejaculation.

For example, U.S. Pat. No. 5,672,612 discloses amorphous paroxetine hydrochloride-ethanol compositions for use as a therapeutic agent for premature ejaculation. This reference also reports that sexual dysfunction typically associated with antidepressants, including delayed and completely abolished ejaculation, has been the subject of numerous case reports, studies, and articles. See, e.g., *Depression*, 2:233-240 (1994/1995); *J. Clin. Psychiatry*, 54:209-212 (1993); *J. Clin. Psychopharmacol.*, 3:76-79 (1983). SSRI antidepressants seem to be a safe treatment option for patients with premature ejaculation, particularly in cases with failed psychological treatment, although other anti-anxiety drugs, such as chlordiazepoxide (LIBRIUM®) and diazepam (VALIUM®) are not suitable for the treatment of premature ejaculation. See also *Clin. Neuropharmacology*, 20(5):466-471 (1997) (treatment of premature ejaculation with fluoxetine) and *Clin. Neuropharmacology*, 20(3):210-214 (mianserin for treatment of sexual dysfunction induced by SSRIs).

U.S. Pat. No. 5,151,448 discloses the chronic administration of fluoxetine, preferably orally, in an amount in the range of about 5 mg to about 80 mg per day, preferably about 20 mg per day for the treatment of premature ejaculation. The compositions are administered for a time period of at least about 3 months, preferably for at least about 6 months. In some instances, fluoxetine is administered chronically as long as the patient remains sexually active.

U.S. Pat. No. 5,276,042 discloses the chronic administration of paroxetine, preferably orally, in an amount in the range of about 3 mg to about 30 mg per day, preferably about 10 mg per day for the treatment of premature ejaculation. The compositions are administered for a time period of at least about 3 months, preferably for at least about 6 months. In some instances, paroxetine is administered chronically as long as the patient remains sexually active.

U.S. Pat. No. 5,597,826 discloses the administration of sertraline and an agonist or antagonist of the serotonin 1 (5-$HT_1$) receptor and the use of such compositions for treating or preventing a condition selected from a large list of disorders including sexual dysfunction, such as premature ejaculation. These compositions are disclosed to be administered daily, for example, one to four times daily.

McMahon reports that 37 potent men with premature ejaculation were treated with 50 mg oral sertraline and placebo in a controlled randomized single-blind crossover trial. Chronic open label treatment was continued in 29 patients that achieved an increase in ejaculatory latency over pretreatment levels with active drug. McMahon, *J. Urology*, 159(6): 1935-1938 (1998). McMahon concluded that sertraline appeared to be a useful and well tolerated oral treatment for premature ejaculation after 1 to 2 weeks, with several patients maintaining that control after chronic treatment for several months.

U.S. Pat. Nos. 5,770,606 and 5,624,677 disclose psychogenic impotence or erectile dysfunction that can be identified in patients and treated, without substantial undesirable side effects, by sublingual administration of apomorphine dosage forms to maintain a plasma concentration of no more than about 5.5 nanograms per mL.

Certain selective serotonin re-uptake inhibitors have been reported as being useful for various indications. For example, U.S. Pat. No. 5,135,947 discloses 1-phenyl-3-naphthalenyloxypropanamines and methods of using the same for treating a variety of disorders that have been linked to decreased neurotransmission of serotonin in mammals, including obesity, depression, alcoholism, pain, memory loss, anxiety, smoking, and the like.

The above-discussed references primarily concern the chronic administration of therapeutic agents for the treatment of premature ejaculation, but do not discuss administration on an as-needed basis. As discussed above, treatment of premature ejaculation can involve administration of certain selective serotonin reuptake inhibitors, such as fluoxetine, paroxetine, or sertraline, to delay ejaculation. This type of drug works by increasing the amount of serotonin in the body and can be administered daily (*Merck Manual of Medical Information* at 421-422, Home Edition, Merck Research Laboratories (1997)).

Paick et al. recently reported that self-therapy with sertraline tablets was investigated by chronic administration followed by as-needed administration on the day of intercourse. Paick, J. S., et al., *J. Urology*, 159(S5):241 (June, 1998). This study was conducted with 24 males for six weeks, and the authors reported that 50 mg doses were administered for 2 weeks followed by self therapy with 50 mg or 100 mg of sertraline as-needed at 5 p.m. in treatment of premature ejaculation. The authors concluded that such therapy could possibly be as attractive as self injection therapy in the treatment of erectile dysfunction.

McMahon and Touma, *J. Urol.*, 161, 1826-1839 (1999) showed in 26 patients suffering from premature ejaculation that prn dosing with 20 mg paroxetine tablet 3-4 hours prior to intercourse resulted in a statistically significant increase in ejaculatory latency in the second through fourth weeks of paroxetine treatment but not in the first week, indicating that 1-2 weeks of "priming doses" of paroxetine are required. Frequency of intercourse was significantly increased only after 3 weeks of prn paroxetine therapy.

In a subsequent paper, McMahon and Touma, *International J. Impotence Research*, 11, 241-246 (1999), showed that 20 mg prn paroxetine improved ejaculatory latency in only 42% of their patients and the increase in ejaculatory was only reported as being statistically significant after 4 weeks of treatment, again indicating the need for "priming doses" of paroxetine. In addition, 37% of patients that initially showed improvement in ejaculatory latency with continuous dosing of paroxetine subsequently lost benefit after switching to prn dosing. Similarly, Salem, et al., *J. Urol*, 163(S4), 197 (2000), showed that 100% of patients that initially showed improvement in ejaculatory latency with continuous dosing of fluoxetine subsequently lost benefit after switching to prn dosing.

Proper treatment of premature ejaculation involves not just inhibiting early ejaculation, but in ensuring that the patient has increased control over the timing of the ejaculation. The available options for treating premature ejaculation also typically require daily dosage to maintain suitable plasma levels. The daily or chronic use of conventional SSRIs and related compounds for such therapy may result in adverse effects expected with high or continuing dosages of such compounds. In addition, chronic or daily administration of conventional SSRIs is a burdensome requirement on the patient. Furthermore, the latency period, from time of dosing to engaging in sexual activity, associated with conventional SSRI's is another hurdle which the patient must deal with. Finally, not experiencing benefit from a drug with a single, or the first, administration of drug is also burdensome. It is thus desired to find a compound and method for sexual dysfunction therapy, in particular, to provide increased control over ejaculatory timing. In particular, it is desired to achieve the beneficial therapeutic effect of preventing, treating, or managing sexual dysfunction while reducing or avoiding adverse effects associated with the present protocols for administration of sexual dysfunction therapy. In particular, it is desirable to consistently achieve the maximum therapeutic response within a convenient time frame following administration of a drug therapy immediately before to 4 hours on an as-needed basis to allow a patient to coordinate drug therapy with the timing of intercourse following a single, or the first, dose.

The invention encompasses methods and compounds employing as-needed dosing, also known as pro re nata dosing (referred to herein as "prn dosing"), to prevent, treat, and manage sexual dysfunction therapy. Without wishing to be bound by theory, it is believed that these methods and compounds provide therapy by accomplishing at least one of the following: increasing the effect of monoamines in the mammal, increasing serotonin in the mammal, or inhibiting or avoiding reuptake of serotonin into nerve terminals in the mammal. Prn dosing reduces and/or avoids adverse effects that can occur with chronic therapy of a therapeutic agent. Thus, the methods of preventing, treating, or managing sexual dysfunction comprise administering a therapeutically effective amount of the active agent to a patient in need of therapy immediately prior to, to about 12 hours prior to, the patient's anticipated sexual activity according to the invention. Preferably a therapeutically effective amount of the active agent is administered to a patient in need of therapy immediately prior to, to about 10 hours prior to, the patient's anticipated sexual activity, more preferably immediately prior to, to about 8 hours prior to, the patient's anticipated sexual activity, and most preferably immediately prior to, to about 4 hours prior to, the patient's anticipated sexual activity. In addition, a therapeutically effective amount of the active agent can be administered to a patient in need of therapy immediately prior to the patient's anticipated sexual activity. Thus, the present invention eliminates the need for chronic or daily administration of the active agent prior to anticipated sexual activity.

Typically, the patient is a mammal, such as a dog, horse, rat, mouse, or human, but in particular, the patient is a human. In a preferred embodiment, the human is male with or at risk of sexual dysfunction, such as premature ejaculation.

One embodiment of the present invention is a method of treating or managing sexual dysfunction in a mammal in need of treatment which comprises administering on an as-needed basis to the mammal a therapeutically effective amount of a rapid-onset selective serotonin reuptake inhibitor. An example of a rapid-onset selective serotonin reuptake inhibitor is dapoxetine or a pharmaceutically acceptable salt thereof. As used herein the term "dapoxetine" refers to the compound of the following formula:

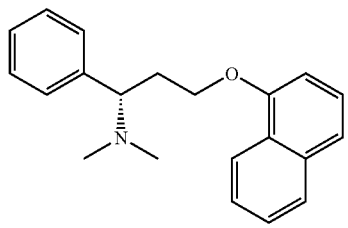

which is also referred to as (S)-(+)-N,N-Dimethyl-1-phenyl-3-(1-naphthalenyloxy)-propanamine or as (S)-(+)-N,N-Dimethyl-α-[2-(1-naphthalenyloxy)ethyl-benzenemethanamine. It is understood by one of ordinary skill in the art that the method of the present invention includes the administration of a rapid-onset selective serotonin reuptake inhibitor, such as dapoxetine as the free base or as a pharmaceutically acceptable salt thereof, such as the HCl salt.

The embodiment preferably encompasses the treatment, prevention, and/or management of such disorders using a single unit dosage form that contains dapoxetine, or a pharmaceutically acceptable salt thereof. The methods of administering dapoxetine, or a pharmaceutically acceptable salt thereof, are also useful in combination with an additional therapeutic agent, such as a conventional selective serotonin reuptake inhibitor (as used herein the term "SSRI" refers to selective serotonin reuptake inhibitor) for the treatment, prevention, or management of sexual dysfunction, such as premature ejaculation. The invention encompasses the treatment, prevention, and/or management of sexual dysfunction and the symptoms thereof using dapoxetine. The invention preferably encompasses the treatment, prevention, and/or management of such disorders using a single unit dosage form that contains dapoxetine, or a pharmaceutically acceptable salt thereof. However, it should be recognized that combination therapy by separate administration of the compositions of the invention and an additional therapeutic agent, such as another SSRI, is also contemplated. The methods and compositions described herein are believed to provide superior or improved therapy over prior art methods and compositions involving paroxetine, fluoxetine, venlafaxine, fluvoxamine, or sertraline in the absence of dapoxetine, or a pharmaceutically acceptable salt thereof.

The present invention further provides a method of treating or managing sexual dysfunction in a mammal in need of treatment which comprises administering on an as-needed basis to the mammal a therapeutically effective amount of a rapid-onset selective serotonin reuptake inhibitor.

The present invention provides an improvement in flexibility of timing with regard to when the therapeutically effective amount of the rapid-onset selective serotonin reuptake inhibitor is taken in relation to the patient's participation in sexual activity, and thus, represents an improvement in the dosing schedule.

The present invention also provides an unexpected benefit with prn dosing with dapoxetine over either prn dosing or continuous dosing with non-rapid onset SSRI's, such as paroxetine, fluoxetine, and sertraline, in that the improvement in ejaculatory latency with prn dosing with dapoxetine occurs after the very first dose or a single dose.

The present invention also shows an improvement in the ability of prn dosed SSRI's, preferably dapoxetine, to treat the full range of PE patients, such as those who consider themselves severe (see tables 13a and 13b) or moderate (see tables 14a and 14b), and patients who have a baseline ejaculatory latency of less than one minute (see tables 10a and 10b) or less than two minutes (see tables 11a and 11b). Dapoxetine also increased ejaculatory latency in patients with baseline latencies greater than or equal to one minute (see tables 16a and 16b) or greater than or equal to two minutes (see tables 15a and 15b). This latter data establishes that administration of a rapid-onset SSRI would be of benefit to a male who does not suffer from premature ejaculation per se, but still wishes to prolong ejaculation.

The present invention provides additional benefit in allowing administration of a therapeutically effective dose of a rapid-onset SSRI, without causing accumulation of the drug when administered on a daily basis, through the drug's demonstration of a short half-life. An example of a rapid-onset SSRI with a short half-life is dapoxetine.

Figure 1:
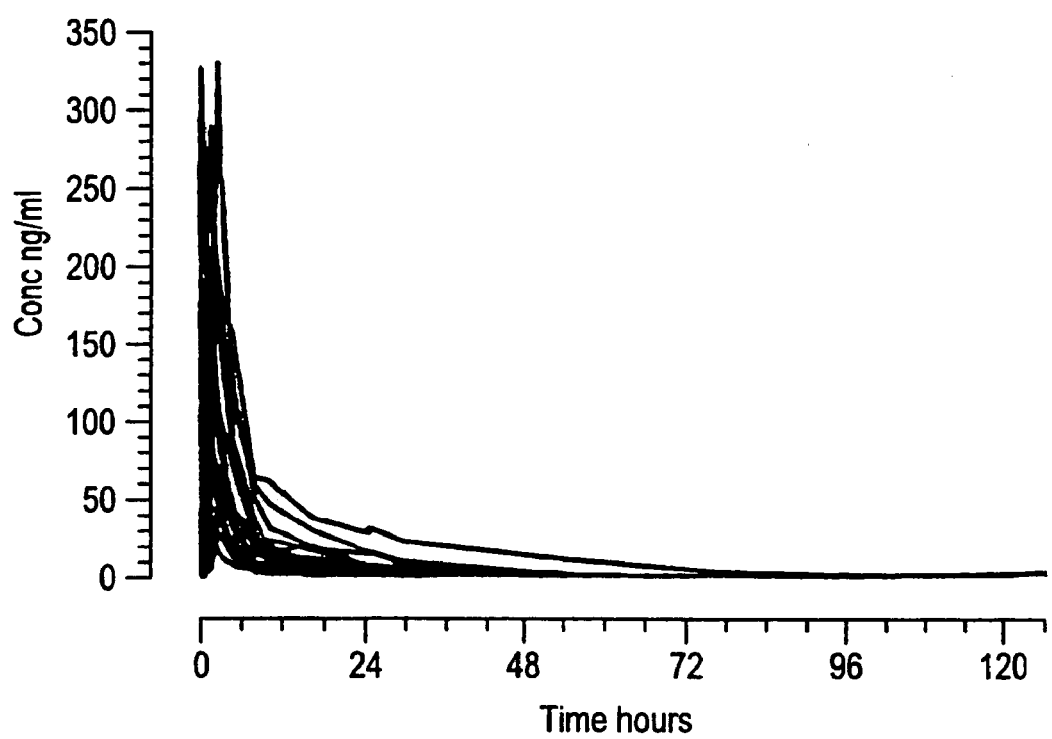
FIG. 1 shows rapid-onset to reach peak plasma concentration followed by rapid metabolism (i.e. short half-life) in 20 volunteers who had taken a dose of 40 mg dapoxetine at time zero of the 14$^{th}$ day of daily dosing.
Figure 2:
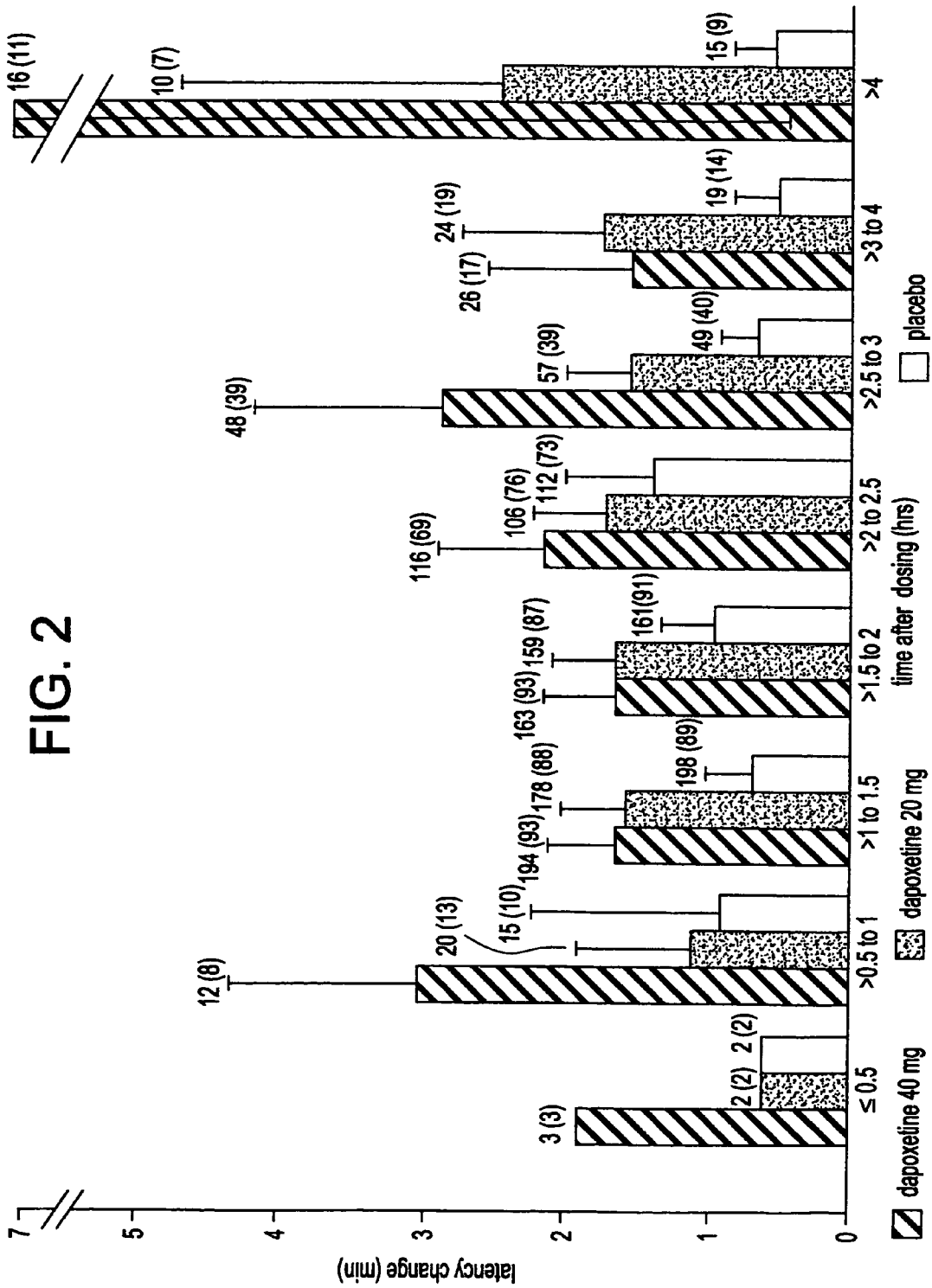
FIG. 2 depicts the ejaculatory latency change in minutes vs. time after dosing for placebo, 20 mg dapoxetine, and 40 mg dapoxetine.

The present invention represents an improvement in overall therapy relative to sexual dysfunction treatment technology presently available.

According to another aspect, the present invention provides the use of a rapid-onset selective serotonin reuptake inhibitor, or a pharmaceutically acceptable salt thereof, on an as-needed basis, for the manufacture of a medicament for treatment or management of sexual dysfunction.

According to yet another aspect, the present invention provides the use of a rapid-onset selective serotonin reuptake inhibitor, or a pharmaceutically acceptable salt thereof, on an as-needed basis, for treatment or management of sexual dysfunction.

The present invention further provides an article of manufacture comprising packaging material and a pharmaceutical agent contained within said packaging material, wherein said pharmaceutical agent is effective for treating premature ejaculation in a human male, and wherein said packaging material comprises a label which indicates that said pharmaceutical agent can be used for treating premature ejaculation in a human male, and wherein said pharmaceutical agent comprises a rapid-onset selective serotonin reuptake inhibitor or a pharmaceutically acceptable salt thereof.

The invention encompasses methods of preventing, treating, or managing sexual dysfunction in a mammal in need of therapy by administering as-needed a therapeutically effective amount of a rapid-onset selective serotonin reuptake inhibitor, or a pharmaceutically acceptable salt thereof. A rapid-onset selective serotonin reuptake inhibitor is administered to a mammal to, for example, increase the effect of monoamines, increase or enhance the effects of serotonin, and/or to inhibit or avoid the reuptake of serotonin into nerve terminals. In particular, the invention encompasses compounds and methods of administering as-needed a therapeutically effective amount of a rapid-onset selective serotonin reuptake inhibitor, or a pharmaceutically acceptable salt thereof, to a human in need of therapy to prevent, treat, or manage sexual dysfunction. A suitable rapid-onset selective serotonin reuptake inhibitor of the present invention is dapoxetine. The invention is discussed in more detail below. For clarity of discussion, the specific example of dapoxetine is used herein to exemplify the use of rapid-onset selective serotonin reuptake inhibitors with the present invention. The present invention also includes rapid-onset selective serotonin reuptake inhibitors that are short acting selective serotonin reuptake inhibitors.

The present invention includes use of dapoxetine, in particular (a) (±)-N,N-dimethyl-1-phenyl-3-(1-naphthalenyloxy)-propanamine, or a pharmaceutically acceptable salt thereof; (b) (S)-(+)-N,N-dimethyl-1-phenyl-3-(1-naphthalenyloxy)-propanamine, (dapoxetine) or a pharmaceutically acceptable salt thereof; and (c) (R)-(−)-N,N-dimethyl-1-phenyl-3-(1-naphthalenyloxy)-propanamine, or a pharmaceutically acceptable salt thereof, as well as any active metabolites thereof. In particular, the active metabolites include, but are not limited to, mono-desmethyl dapoxetine and di-desmethyl dapoxetine. Typically, the compound administered will include only one of these alternative forms, but may include more than one in varying amounts.

As used herein the terms "Me", "Et", "Pr", EtOAc", "THF", and "DMF" refer to methyl, ethyl, propyl, ethyl acetate, tetrahydrofuran and dimethylformamide respectively.

As used herein the term "sexual activity" refers to an activity involving sexual arousal wherein the patient desires to avoid sexual dysfunction, such as premature ejaculation. Examples of sexual activity are intercourse, masturbation, sexual intercourse, and the like. Sexual intercourse is preferred.

As used herein the term "sexual arousal" refers to engorgement of a sexual organ. Examples of sexual organs are the penis and clitoris.

As used herein the term "engorgement" refers to an increase in blood flow to a sexual organ.

As used herein the term "intercourse" refers to physical stimulation between individuals that involves the genitalia of at least one person, such as intromission.

As used herein the term "intromission" refers to the insertion or period of insertion of the penis into an orifice. An example of an orifice is the vagina.

As used herein the term "a rapid-onset selective serotonin reuptake inhibitor" refers to a drug with a pharmacokinetic profile wherein Tmax is consistently less than about 4 hours. In alternative embodiments, "a rapid-onset selective serotonin reuptake inhibitor" refers to a drug with a pharmacokinetic profile wherein Tmax is consistently less than about 3 hours or consistently less than about 2 hours. Dapoxetine is an example of a rapid-onset selective serotonin reuptake inhibitor.

As used herein the term "a short acting selective serotonin reuptake inhibitor" refers to a drug with a pharmacokinetic profile wherein $T_{1/2}$ is less than about 20 hours. In alternative embodiments, "a short acting selective serotonin reuptake inhibitor" refers to a drug with a pharmacokinetic profile wherein $T_{1/2}$ is less than about 13 hours or less than about 7 hours.

The term "racemic" as used herein, means a mixture of the (R) and (S) enantiomers of a compound where the (R) and (S) enantiomers are present in approximately a 1:1 ratio.

The term "substantially free of its (R) stereoisomer" as used herein, means for example, that the compound contains a significantly greater proportion of dapoxetine in relation to its (R) stereoisomer. In a preferred embodiment of the present invention, the compound contains at least about 90% by weight of dapoxetine and about 10% by weight or less of its (R) stereoisomer. In a more preferred embodiment of the present invention, the term "substantially free of its (R) stereoisomer" as used herein, means that the compound contains at least about 95% by weight of dapoxetine and about 5% by weight or less of its (R) stereoisomer. In a most preferred embodiment, the term "substantially free of its (R) stereoisomer" as used herein, means that the compound contains at least about 99% by weight of dapoxetine and about 1% or less of its (R) stereoisomer. In a most especially preferred embodiment, the term "substantially free of its (R) stereoisomer" as used herein, means that the compound contains nearly 100% by weight of dapoxetine.

The term "substantially free of its (S) stereoisomer" as used herein, means for example, that the compound contains a significantly greater proportion of (R)-(−)-N,N-dimethyl-1-phenyl-3-(1-naphthalenyloxy)-propanamine in relation to its (S) stereoisomer. In a preferred embodiment of the present invention, the compound contains at least about 90% by weight of (R)-(−)-N,N-dimethyl-1-phenyl-3-(1-naphthalenyloxy)-propanamine and about 10% by weight or less of its (S) stereoisomer. In a more preferred embodiment of the present invention, the term "substantially free of its (S) stereoisomer" as used herein, means that the compound contains at least about 95% by weight of (R)-(−)-N,N-dimethyl-1-phenyl-3-(1-naphthalenyloxy)-propanamine and about 5% by weight or less of its (S) stereoisomer. In a most preferred embodiment, the term "substantially free of its (S) stereoisomer" as used herein, means that the compound contains at least about 99% by weight of (R)-(−)-N,N-dimethyl-1-phenyl-3-(1-naphthalenyloxy)-propanamine and about 1% or less of its (S) stereoisomer. In a most especially preferred embodiment, the term "substantially free of its (S) stereoisomer" as used herein, means that the compound contains nearly 100% by weight of (R)-(−)-N,N-dimethyl-1-phenyl-3-(1-naphthalenyloxy)-propanamine(R)-(−)-N,N-dimethyl-1-phenyl-3-(1-naphthalenyloxy)-propanamine.

Dapoxetine and its pharmaceutically acceptable salts can be readily prepared by procedures well known to those of ordinary skill in the art. See for example U.S. Pat. No. 5,135,947, issued Aug. 4, 1992 the disclosure of which is incorporated herein by reference. In addition, for preparation of various useful intermediates of dapoxetine, see U.S. Pat. No. 5,292,962, issued Mar. 8, 1994 the disclosure of which is incorporated herein by reference.

In one embodiment of the present invention, a rapid-onset selective serotonin reuptake inhibitor or a pharmaceutically acceptable salt thereof can be administered to an animal in combination with a compound capable of increasing or enhancing the effect of monoamines or serotonin in the mammal is suitable for use in the methods and compounds of the present invention. Preferred monoamine-increasing compounds include, but are not limited to, amitriptyline (ELAVIL™ and VANATRIP™), amitriptyline and chlordiazepoxide (LIMBITROL™), amitriptyline and perphenazine (ETRAFON™ and TRIAVIL™), amoxapine (ASENDIN™), clomipramine (ANAFRANIL™), citalopram (CELEXA™), dapoxetine, desipramine (NORPRAMIN™ and PERTOFRANE™), doxepin (ADAPIN™, SINEQUAN™, XEPIN™, and ZONALON™), duloxetine, fluoxetine (PROZAC™), fluvoxamine (LUVOX™), imipramine (JANIMINE™, TOFRANIL™, and TOFRANIL-PM™), isocarboxazid (MARPLAN™), mirtazapine (REMERON™), nortriptyline (PAMELOR™), paroxetine (PAXIL™), phenelzine (NARDIL™), protriptyline (VIVACTIL™), refazodone (SERZONE™), selegiline (ALZENE™, CARBEX, DEPRENYL™, and ELDEPRYL™), sertraline (ZOLOFT™), tranylcypromine (PARNATE™), trazadone (DESYREL™), trimipramine (SURMONTIL™), and venlafaxine (EFFEXOR™).

It should also be recognized for all embodiments herein that combination therapy by separate administration of the compounds of the invention and an additional therapeutic agent, such as one or more drugs (e.g., yohimbine) for a second, different sexual dysfunction is also contemplated.

The various compounds enumerated above with a tradename are generally commercially available. The remaining compounds may be readily prepared or obtained by those of ordinary skill in the pharmaceutical art. For example, one of ordinary skill in the art is readily able to synthesize dapoxetine, or a pharmaceutically acceptable salt thereof, as well as metabolites or the optically pure stereoisomers or salts thereof, for use in the compounds and methods of the invention, such as by following the teachings of U.S. Pat. No. 5,135,947. See also W. J. Wheeler, et al., "A Chiral Synthesis of Dapoxetine Hydrochloride, a Serotonin Re-uptake Inhibitor, and its $^{14}$C Isotopomer," *J. Labeled Compounds Radiopharmaceuticals*, 31(4):305-315 (1992).

The terms "composition(s)," "active agent(s)," and "compound(s)," as used herein, each encompass a: (a) composition(s) to increase the effect of monoamines; (b) composition(s) to increase serotonin in the mammal; (c) composition(s) that inhibit or avoid the reuptake of serotonin into nerve terminals in the mammal; and (d) serotonin-selective re-uptake inhibitor(s); or a pharmaceutically acceptable salt thereof. The terms "composition(s)," "active agent(s)," and "compound(s)" also include any optically pure isomer, or a pharmaceutically acceptable salt thereof, as well as any active metabolite, or a pharmaceutically acceptable salt thereof, of the above-noted compound(s).

The term "additional therapeutic agent(s)," as used herein, refers to the use of compounds that may be used in addition to the compound to prevent, treat, or manage sexual dysfunction in a patient in need of therapy. For example, yohimbine or nitric oxide may be used for erectile dysfunction therapy in addition to a compound as discussed herein according to the invention. Other suitable additional therapeutic agents include, but are not limited to, eicosanoids, such as alprostadil, and phosphodiesterase inhibitors, such as sildenafil citrate (VIAGRA®) and IC 351.

The term "pharmaceutically acceptable salt" as used herein, refers to salts of the compounds disclosed herein which are substantially non-toxic to living organisms. Typical pharmaceutically acceptable salts include those salts prepared by reaction of the compounds of the present invention with a pharmaceutically acceptable mineral or organic acid. Such salts are known as acid addition salts. Pharmaceutically acceptable salts also include compounds that have been formulated to have a Tmax of less than about 4 hours.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

The pharmaceutical compounds used in the methods of the present invention, which are sterile where appropriate, include any of the above-listed compounds, or a pharmaceutically acceptable salt thereof, as the active ingredient. The compounds may also contain a pharmaceutically acceptable carrier or excipient, and optionally, other therapeutic ingredients.

The compounds for use in the methods of the present invention can include suitable excipients or carriers such as starches, sugars, microcrystalline cellulose, diluents, granulating agents, lubricants, binders, disintegrating agents, and the like. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

Dosage forms include tablets, troches, dispersions, suspensions, solutions, capsules, caplets, cachets, patches, gel caps, syrups, elixirs, gels, powders, magmas, lozenges, ointments, creams, pastes, plasters, lotions, discs, suppositories, nasal or oral sprays, aerosols, and the like.

Because of their ease of administration, tablets and capsules represent the most advantageous oral dosage unit form, in which case solid pharmaceutical carriers are employed. If desired, tablets may be coated by standard aqueous or non-aqueous techniques.

In addition to the common dosage forms set out above, the compounds of the present invention may also be administered to facilitate as-needed administration by controlled release means or delivery devices that are well known to those of ordinary skill in the art, such as those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are each incorporated herein by express reference thereto. These pharmaceutical compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art, including those described herein, may be readily selected for use with the pharmaceutical compounds and methods of the invention. Thus, single unit dosage forms suitable for oral administration, such as tablets, capsules, gelcaps, caplets, and the like, that are adapted for controlled-release are encompassed by the present invention. The term "controlled-release formulation(s)," as used herein, means a formulation adapted to provide extended release of the active ingredient(s) during the need for therapy. For example, but in no way intended to limit the invention, a controlled-release formulation according to the invention might release active ingredient(s) over a 2 to 8 hour period of time.

All controlled-release pharmaceutical products have a common goal of improving drug therapy over that achieved by their non-controlled counterparts. Ideally, the use of an optimally designed controlled-release preparation in medical treatment according to the invention is characterized by a minimum of drug substance being employed to cure or control the condition during the need for therapy. Advantages of controlled-release formulations according to the invention may include: 1) activity of the drug that is extended for the duration of the need for therapy; 2) reduction of peak plasma concentration of the active ingredient(s); and 3) increased patient compliance.

Most controlled-release formulations are designed to initially release an amount of drug that promptly produces the desired therapeutic effect, and gradually and continually release of other amounts of drug to maintain this level of therapeutic effect over a period of time sufficient to provide the as-needed therapy. In order to maintain this constant level of drug in the body while needed for therapy, the drug must be released from the dosage form at a rate that will replace the amount of drug being metabolized and excreted from the body. The drug must also be released at a sufficient rate to facilitate absorption into the bloodstream during the need for therapy.

The controlled-release of an active ingredient may be stimulated by various inducers, for example pH, temperature, enzymes, water, or other physiological conditions or compounds. The term "controlled-release component," as used herein, means a compound or compounds, including, but not limited to, polymers, polymer matrices, gels, permeable membranes, liposomes, microspheres, or the like, or a combination thereof, that facilitates the controlled-release of the active ingredient as-needed for therapy.

In addition, it is understood that the compounds of the present invention may be administered as rapidly disintegrating or dissolving pharmaceutical dosage forms which are readily prepared by one of ordinary skill in the art. Such formulations are useful, for example, for human patients who have difficulty swallowing conventional tablets or capsules, and are also useful for the sublingual and buccal administration of drugs.

Observations from the final analyses of the study cited in the example section allow one to predict that a non-rapid onset SSRI formulated to provide rapid-onset selective would be expected to provide substantial benefit over current formulations of non-rapid onset SSRI's. Thus, a further embodiment of the present invention is the delivery of a non-rapid onset SSRI, such as fluoxetine, paroxetine, or sertraline, in a rapid release formulation.

For example, freeze-dried or lyophilized dosage forms are generally known to rapidly dissolve or disintegrate in the mouth. These forms consist of a porous matrix of a water-soluble or water-dispersible carrier material which is impregnated with a unit dose of the active compound. These dosage forms are prepared by first adding the active compound to a solution comprising the carrier material and a suitable solvent, typically water. The resulting composition is then subjected to a freeze drying procedure whereby the solvent sublimes under a high vacuum.

In addition, U.S. Pat. No. 4,866,046, issued Sep. 12, 1989, describes an aspirin tablet, for example, that rapidly dissolves in the oral, preferably sublingual, cavity within 2-60 seconds. This tablet provides rapid absorption of aspirin from the saliva into the blood stream. The sublingual tablet is prepared by compressing into slugs a mixture of starch (10% moisture), acetylsalicylic acid, flavor and sweetener. The slugs are then ground (14-16 Mesh size) and recompressed into tablets. An amino acid may also be used with the aspirin for its solubilizing and a taste-neutralizing effects.

U.S. Pat. No. 5,082,667, issued Jan. 21, 1992, discusses a tablet triturate dosage that dissolves quickly in the buccal cavity. The form includes a porous, cementatory network of a water-soluble but ethanol-insoluble carbohydrate, which contains discrete particles of the active compound that have been coated with a triglyceride coating. The discrete particles are prepared by suspending the active ingredient in molten triglyceride. The discrete particles are mixed with the carbohydrate and a temporary liquid binder to form a damp mass. The mass is then shaped into a tablet and dried to form the tablet triturate. This tablet triturate method is limited, however, to active compounds, that are not sensitive to the melting temperature of the triglyceride.

Pharmaceutical compositions for use in the methods of the present invention may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form, such as powder or granules, optionally mixed with a binder, lubricant, inert diluent, surface active or dispersing agent. Molded tablets may be made by molding, in a suitable machine, a mixture of the powdered compound moistened with an inert liquid diluent.

The administration of these compositions in the methods of the present invention may be either concurrent or sequential, e.g., a rapid-onset selective serotonin reuptake inhibitor, or a pharmaceutically acceptable salt thereof, may be administered as a combination (a single unit dosage), or concurrently but separately, with one or more additional therapeutic agents, such as one or more drugs for erectile dysfunction or low libido, for the prevention, treatment, or management of sexual dysfunction. The compounds of the invention may also be provided by the sequential administration of one of the compounds discussed above and one or more additional therapeutic agents suitable for the prevention, treatment, or management of a sexual dysfunction in any possible order. The compositions administered in each of these methods may be concurrent, sequential, or in any combination of concurrent and/or sequential.

The terms "as-needed," "as-needed basis," "prn," and "prn dosing," as used herein, mean administering a therapeutically effective amount of a rapid-onset selective serotonin reuptake inhibitor according to the invention at a time interval sufficient to provide an improved therapeutic profile, i.e., improved therapy, in the prevention, treatment, or management of sexual dysfunction while avoiding priming doses, chronic administration, and/or overdosing. As used herein, the term "therapeutically effective amount," means the amount of a rapid-onset selective serotonin reuptake inhibitor or a pharmaceutically acceptable salt thereof, that provides a therapeutic benefit in the treatment, prevention, or management of one or more sexual dysfunctions or the symptoms of the one or more sexual dysfunctions. The term "sexual dysfunction," as used herein, includes, but is not limited to, premature ejaculation, retarded ejaculation (male), inhibited orgasm (female), low sexual desire, sexual aversion, dyspareunia, and vaginismus. In particular, sexual dysfunction means premature ejaculation. The term "premature ejaculation," as used herein, means intravaginal ejaculation latency of less than 2 minutes that occurred in greater than 50% of intercourse for at least the previous 6 months. The term is also used in accordance with DSM IV to mean: (1) persistent or recurrent ejaculation with minimal sexual stimulation before, on, or shortly after penetration and before the person wishes it, which must account for factors that affect duration of the excitement phase, such as age, novelty of the sexual partner or situation, and recent frequency of sexual activity; (2) the disturbance causes marked distress or interpersonal difficulty; and (3) the premature ejaculation is not due exclusively to the direct effects of a substance (e.g., withdrawal from opioids).

One embodiment of the present invention is prn dosing of a rapid-onset selective serotonin reuptake inhibitor, or a pharmaceutically acceptable salt thereof, prior to sexual activity. A preferred method includes prn dosing of a rapid-onset selective serotonin reuptake inhibitor from immediately prior to, to about 12 hours prior to, sexual activity. A more preferred method includes prn dosing immediately prior to, to about 10 hours prior to, sexual activity. A more preferred method includes prn dosing immediately prior to, to about 8 hours prior to, sexual activity. A most especially preferred method includes prn dosing immediately prior to, to about 4 hours prior to, sexual activity.

Those of ordinary skill in the art are well aware of a suitable time interval for dosing purposes as discussed herein, which may depend on other therapeutic compositions being taken by the patient. By way of example, and in no way intended to be limiting, a suitable time interval might be about 1 to 4 hours prior to the need for therapy, but not more than once per day.

The amount of a dose of a rapid-onset selective serotonin reuptake inhibitor, or a pharmaceutically acceptable salt thereof, in prn dosing is an amount suitable for management of a disorder or condition. The amount will vary with the severity of the condition to be treated and the route of administration. The dose and dose frequency will also vary according to the age, body weight, and response of the individual patient. A suitable dose range can be readily determined by one of ordinary skill in the art. In general, the total dose for a rapid-onset selective serotonin reuptake inhibitor, or a pharmaceutically acceptable salt thereof, for the conditions described herein, ranges from about 0.001 mg to about 350 mg, preferably from about 0.01 mg to about 200 mg, more preferably from about 0.01 mg to about 120 mg, and most especially preferred about 1 mg to about 80 mg, administered in single or divided doses as needed. These dosages are preferably adapted for self-administration as-needed by the patient.

It is further recommended that patients aged over 65 years, and those with impaired renal or hepatic function, initially receive low doses, and that they then be titrated based on individual response(s) or blood level(s). It may be necessary to use dosages outside these ranges in some cases, as will be apparent to those skilled in the art. Further, it is noted that the clinician or treating physician will know how and when to adjust, interrupt, or terminate therapy in conjunction with individual patient response.

The efficacy of a prn dosing method of the present invention can be tested in a variety of ways. For example, a skilled artisan could compare responses with and without administration of a prn dose of dapoxetine, or a pharmaceutically acceptable salt thereof, (within a time frame compatible with the pharmacokinetics of dapoxetine). Suitable responses to compare include, for example, determining latency from initiation of sexual activity until time of ejaculation with a chronometer, by determining the number of pelvic thrusts associated with intercourse, by counting the number of times ejaculation occurs prior to penetration, or through the use of a question or series of questions posed to the patients.

The efficacy of a prn dosing method with dapoxetine, or a pharmaceutically acceptable salt thereof, can be determined, for example, as follows. In Vivo testing of human subjects can be conducted via a double-blind, randomized, placebo-controlled safety and efficacy study at 2 to 15 sites. To ensure 128 evaluable Subjects, approximately 168 Subjects can be randomized to one of four treatments: placebo, 20 mg or 40 mg dapoxetine. The study can include a screening visit, a lead-in period of 4 weeks or less in which intercourse was attempted at least 4 times, and a treatment period of 4 weeks or less in which intercourse was attempted at least 4 times. Subjects should be healthy men at least 18 years of age with a diagnosis of premature ejaculation.

Subjects should be instructed to take study medication (one dose is 2 tablets of either placebo, 10 mg or 20 mg dapoxetine) within 1-3 hours of anticipated sexual activity. Study medication is not taken more than 1 time per day. Subjects can be stratified at the time of enrollment in a 1:1:1 ratio of placebo and 2 doses of dapoxetine. Efficacy of dapoxetine, or a pharmaceutically acceptable salt thereof, can be assessed by comparing ejaculatory latencies recorded with a stopwatch by the partner and recorded in an event log.

The patient-perceived-benefit of prn dosing method with dapoxetine, or a pharmaceutically acceptable salt thereof, can be determined, for example, through administration of a global satisfaction question, such as:

"How would you complete the following statement?

The new bottle of medication that I received at my previous visit made my premature ejaculation problem:
_ much better
_ better
_ slightly better
_ the same
_ slightly worse
_ worse
_ much worse"

In addition, the patient-perceived-benefit of prn dosing method with dapoxetine, or a pharmaceutically acceptable salt thereof, can be determined, for example, through administration of a psychometric quality of life instrument, such as a premature ejaculation questionnaire (PEQ).

Subjects should be healthy men at least 18 years of age with a diagnosis of premature ejaculation as defined by DSM IV. Subjects who meet the selection criteria can provide a medical history and have psychosexual and physical examinations at screening. Efficacy of dapoxetine, or a pharmaceutically acceptable salt thereof, can be assessed by comparing ejaculatory latencies recorded with a stopwatch by the partner and recorded in an event log. Safety can be assessed by clinical laboratory analyses, vital signs, and adverse experience reports collected throughout the study. A physical examination, including chest x-ray and ECG, can be performed at the final visit.

Each subject should comply with the following criteria, premature ejaculation as defined in the DSM IV or intravaginal ejaculation latency over 2 minutes that occurred in over 50% of intercourse for at least the previous 6 months, as noted by both Subject and Partner/Spouse. Criteria for Premature Ejaculation should be as follows: (1) persistent or recurrent ejaculation with minimal sexual stimulation before, on, or shortly after penetration and before the person wishes it. The clinician must take into account factors that affect duration of the excitement phase, such as age, novelty of the sexual Partner or situation, and recent frequency of sexual activity; (2) the disturbance causes marked distress or interpersonal difficulty; and (3) the premature ejaculation is not due exclusively to the direct effects of a substance (e.g., withdrawal from opioids). Subjects in the study should be heterosexual male, at least 18 years of age in a stable, monogamous, sexual relationship for at least 6 months. The Subject and Partner/Spouse should both agree to attempt at least 4 vaginal intercourses between visit 1 and visit 2 (which can be no longer than 4 weeks time) and 4 vaginal intercourses between visit 2 and visit 3, visit 3 and visit 4, and visit 4 and visit 5 (none of which can be longer than 4 weeks time). The Subject and Partner should be capable of understanding and complying with the protocol and both have understood and signed the informed consent document. If Partner/Spouse is of child-bearing potential (i.e., not postmenopausal or not surgically sterile) and Subject is not sterile, Subject and/or Partner should use an acceptable form of birth control (condom, oral contraceptives). Subject and Partner should agree to use the same form of birth control throughout the study. Subjects meeting any of the following criteria should be excluded from the study, any clinically significant abnormalities, history or presence of cardiac or vascular disease, hypertension, hepatic, renal pulmonary, neurological or endocrinologic diseases, significantly abnormal ECG at Screening, a history of alcohol/drug abuse within previous 6 months; average consumption of more than 2 drinks per day, a presence of major psychiatric disorders (e.g., schizophrenia, depression), concurrent erectile dysfunction, urethritis, chronic prostatitis, pelvic surgery or trauma/injury to spinal cord, positive hepatitis B surface antigen (HB sAg), HCV, or human immunodeficiency virus (HIV) test results, has a known hypersensitivity to dapoxetine or other SSRIs, has received any investigational drugs within the previous 30 days, is unwilling or unable to cooperate fully with the Investigator, is taking the anti-hypertensive drugs, guanethidine or reserpine, or has evidence of any medical condition that would interfere with premature ejaculation, such as Subjects taking any of the medications within the stated washout period listed below in Table 1.

TABLE 1

| Medications | |
| --- | --- |
| Medication/Treatment | Washout Period |
| Over the counter cough/cold preparations | 7 days |
| Antiepileptics (e.g., phenytoin) | 30 days |
| Antispasmodics (e.g., procyclidine) | 30 days |
| Barbiturates (e.g., phenobarbital) | 30 days |
| Cimetidine | 30 days |
| Other Investigational Drugs | 30 days |

TABLE 1-continued

| Medications | |
| --- | --- |
| Medication/Treatment | Washout Period |
| Prescription or over the counter diet medications or treatments | 30 days |
| Sedating antihistamines | 30 days |
| Wartarin-like compounds (e.g., Coumadin) | 30 days |
| Lithium | 30 days |
| Selective Serotonin Re-uptake Inhibitors [SSRIs] (e.g., ZOLOFT, PAXIL, PROZAC] | 30 days |
| Tncyclicm Antidepressants (e.g., Coxefen, Nortriptylene, Amitriptyline) | 30 days |
| Monoamine Oxidase Inhibitors [MAOIs] (Nardil, Pamate, etc.) | 30 days |
| Antihypertensives: α-blockers; clonidine; α-methyl DOPA, or β-blockers | 30 days |

Subjects can be stratified at the time of enrollment in a 1:1:1 ratio of placebo and 2 doses of dapoxetine. Both the Investigator and Subject should be blinded from study drug assignment.

Vital signs assessments include blood pressure, heart rate, respiration, and body temperature and these can be determined at Screening and visits 2, 3, 4, and 5. Blood pressure and heart rate measurements can be obtained with the Subject recumbent and sitting. Oral body temperature (degrees Fahrenheit) may be measured as part of each set of vital sign measurements specified above. Laboratory analysis of standard assays can be done at Screening and visits 2, 3, 4, and 5. Patients can be given event logs and stopwatches at visit 1 to record the time study medication is taken, when intercourse is attempted, and the ejaculatory latency, defined as the time from intromission to ejaculation. The patient and partner can initial each event in the event log. Questionnaires should be administered at visits 1, 2, 3, 4, and 5 at the investigative site.

Subjects can be given 6 doses of study drug (i.e., 12 capsules) at visit 2. Subjects should self-administer the study medication within 1-3 hours of anticipated sexual activity. The study drug should not be taken more than one time per day. Dosing can be captured by the Subject in his event log. Dosing information in the Subject's event log can be compared to the amount of drug left at visit 3.

Subjects can not take any of the medications listed in the table in the Exclusion Criteria section within the specified washout period. Subjects should not take new medications (i.e., medications started within 30 days prior to study start or at some point during the study) or stop taking any medications during the course of this study. Use of all medications (over-the-counter, prescription, and herbal) can be recorded on the concomitant medication page of the case report form.

Comparisons can be made between absolute values for placebo-treated versus each of the dapoxetine-treated groups.

Subjects can be required to attempt intercourse on at least 4 occasions across a maximum time period of 4 weeks during the lead-in period. After 4 attempts at intercourse, the subjects should return for visit 2. Event logs should be collected, subject/partner global satisfaction recorded, and the quality of life questionnaire administered. The subject should be randomized to one of 18 dosing regimens of placebo or dapoxetine (20 or 40 mg prn). After 4-6 attempts at intercourse across a maximum time period of 4 weeks, the subject should return for visit 3. Event logs should be collected, subject/partner global satisfaction recorded, and the quality of life questionnaire administered. The next dose of placebo or dapoxetine should then be distributed. After 4-6 attempts at intercourse across a maximum time period of 4 weeks, the subject should return for visit 4. This pattern can be repeated until the patient has received placebo and both doses of dapoxetine.

Measures for "ejaculatory latency" and "number of thrusts prior to ejaculation" should be recorded as the average of the 4-6 events recorded in the event logs for that treatment period. Subjects who ejaculated prior to intromission should have a zero recorded for both "ejaculatory latency" and "number of thrusts prior to ejaculation." "Measures for Subject and Partner satisfaction scores (global impression)" and "Subject and Partner ejaculatory (or sexual) quality-of-life questionnaire" for each treatment period should be based on the score collected at the visit immediately following each treatment period.

Capsules or tablets can be prepared that contain placebo, 10 mg or 20 mg dapoxetine. Two capsules or two tablets should be taken by a Subject 1-3 hours prior to anticipated sexual activity. Other suitable oral formulations for the present invention are listed in Tables 2, 3, 4, 5, 6 and 7.

TABLE 2

Oral Formulation

| Component | 5 mg capsule | 10 mg capsule | 20 mg capsule |
|---|---|---|---|
| Dapoxetine | 5.0 | 10.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The active ingredient (e.g., dapoxetine, or a pharmaceutically acceptable salt thereof) can be sieved and blended with the excipients listed. The mixture can be filled into suitably sized two-piece hard gelatin capsules using suitable machinery and methods well known in the art. See Remington's Pharmaceutical Sciences, 16th or 18th Editions, each incorporated herein in its entirety by this reference. Other doses may be prepared by altering the fill weight and, if necessary, changing the capsule size to suit.

TABLE 3

Compressed Tablet Unit Dosage Forms

| Component | 2.5 mg tablet | 5.0 mg tablet | 20 mg tablet |
|---|---|---|---|
| Dapoxetine | 2.5 | 5.0 | 20.0 |
| Microcrystalline Cellulose | 90.0 | 90.0 | 90.0 |
| Pre-gelatinized Starch | 100.3 | 97.8 | 82.8 |
| Croscarmellose | 7.0 | 7.0 | 7.0 |
| Magnesium Stearate | 0.2 | 0.2 | 0.2 |

The active ingredient (e.g., dapoxetine, or a pharmaceutically acceptable salt thereof) can be sieved through a suitable sieve and blended with the excipients until a uniform blend is formed. The dry blend can be screened and blended with the magnesium stearate. The resulting powder blend can then be compressed into tablets of desired shape and size. Tablets of other strengths can be prepared by altering the ratio of the active ingredient to the excipient(s) or modifying the table weight.

TABLE 4

Tablets

| | Quantity per Tablet in mg. | | |
|---|---|---|---|
| Formula | A | B | C |
| Active Ingredient: Dapoxetine | 5.0 | 10.0 | 25.0 |
| Lactose BP | 62.0 | 107.0 | 137.0 |
| Starch BP | 20.0 | 20.0 | 25.0 |
| Microcrystalline Cellulose | 10.0 | 10.0 | 10.0 |
| Hydrogenated Vegetable Oil | 1.5 | 1.5 | 1.5 |
| Polyvinylpyrrolidinone | 1.5 | 1.5 | 1.5 |
| Compression Weight | 100.0 | 150.0 | 200.0 |

The active ingredient (e.g., dapoxetine, or a pharmaceutically acceptable salt thereof) can be sieved through a suitable sieve and blended with the lactose until a uniform blend is formed. Suitable volumes of water are added and the powders are granulated. After drying, the granules are then screened and blended with the remaining excipients. The resulting granules are then compressed into tablets of desired shape. Tablets of other strengths can be prepared by altering the ratio of active ingredient to the excipient(s) or the compression weight.

TABLE 5

Tablets

| | Quantity per Tablet in mg. | | |
|---|---|---|---|
| Formula | A | B | C |
| Active Ingredient: Dapoxetine | 5.0 | 10.0 | 25.0 |
| Lactose BP | 48.5 | 93.5 | 83.5 |
| Starch BP | 30.0 | 30.0 | 60.0 |
| Pregelatinized Maize Starch BP | 15.0 | 15.0 | 15.0 |
| Magnesium stearate BP | 1.5 | 1.5 | 1.5 |
| Compression Weight | 100.0 | 150.0 | 540.0 |

The active ingredient (e.g., dapoxetine, or a pharmaceutically acceptable salt thereof) can be sieved through a suitable sieve and blended with lactose, starch, and pregelatinized maize starch until a uniform blend is formed. Suitable volumes of water are added and the powders are granulated. After drying, the granules are then screened and blended with the remaining excipients. The resulting granules are then compressed into tablets of desired shape. Tablets of other strengths can be prepared by altering the ratio of active ingredient to excipient(s) or compression weight.

TABLE 6

Tablets

| | Quantity per Tablet in mg. | | |
|---|---|---|---|
| Formula | A | B | C |
| Active Ingredient: (R)-(−)-N,N-Dimethyl-1-phenyl-3-(1-naphthalenyloxy)-propanamine | 5.0 | 10.0 | 25.0 |
| Lactose BP | 48.5 | 43.5 | 78.5 |
| Starch BP | 30.0 | 30.0 | 30.0 |
| Pregelatinized Maize Starch BP | 15.0 | 15.0 | 15.0 |
| Magnesium stearate BP | 1.5 | 1.5 | 1.5 |
| Compression Weight | 100.0 | 100.0 | 100.0 |

The active ingredient, (R)-(−)-N,N-Dimethyl-1-phenyl-3-(1-naphthalenyloxy)-propanamine, can be sieved through a suitable sieve and blended with lactose, starch, and pregelatinized maize starch until a uniform blend is formed. Suitable volumes of water are added and the powders granulated. After drying, the granules are screened and blended with the remaining excipients. The resulting granules are then compressed into tablets of desired shape. Tablets of other strengths can be prepared by altering the ratio of active ingredient to the excipient(s) or the compression weight.

TABLE 7

Composition of placebo, 10 mg Dapoxetine, 20 mg Dapoxetine, and 30 mg Dapoxetine Capsules.

| Ingredient | Placebo | 10 mg Capsule | 20 mg Capsule | 30 mg Capsule |
| --- | --- | --- | --- | --- |
| Dapoxetine HCl (mg) | NA | 11.351 | 22.702 | 34.053 |
| Starch, pregelatinized, NF (Starch 1500) (mg) | 223.31 | 211.959 | 200.608 | 189.257 |
| Dimethicone, NF (mg) (Dow Corning 360 Medical Fluid, 350 cs) | 1.69 | 1.69 | 1.69 | 1.69 |
| Total Fill Weight per Capsule (mg) | 225 | 225 | 225 | 225 |

*The amounts of dapoxetine HCl are equivalent to the corresponding potencies (10 mg, 20 mg, and 30 mg) of the free base, dapoxetine.

Table 7 provides an additional formulation for the placebo and the 10 mg, 20 mg, and 30 mg capsules of dapoxetine. Dapoxetine HCl is blended with the excipients listed in table 7 under conditions and using techniques well known to one of ordinary skill in the art. The mixture is then filled into suitably sized hard gelatin capsules using suitable machinery and methods well known in the art.

The Investigator can give the Subject 12 capsules of study drug at each visit beginning with visit 2 and ending with visit 4. Twelve capsules should be sufficient supply for the target of 4 attempts at intercourse (8 capsules) plus 2 planned, but aborted, attempts (4 "extra" capsules). At each subsequent visit, Subjects should return unused study medication from the previous treatment period and can be given the next 12 capsules (containing a different dosage from the previous study periods) of study drug. The Subject should be allowed a maximum of one dose (two capsules) per day. Drug administration should be recorded by the Subject in his event log. Investigator should maintain a dispensing and an inventory record of all test articles during the study and should compare amount of study medication returned at these visits to drug administration record in the Subject's event log. Any unused test articles should be returned to the sponsor at the end of the study.

After first treatment period, patient can be crossed over to a different dose of study medicine (placebo, 20 mg or 40 mg dapoxetine). After the second treatment period, patient can be crossed over to the final study medicine (placebo, 20 mg or 40 mg dapoxetine).

Any suitable route of administration may be employed for providing a mammal with an effective dosage of dapoxetine according to the methods of the present invention. For example, oral, rectal, parenteral, epicutaneous, transdermal, subcutaneous, intramuscular, intranasal, sublingual, buccal, intradural, intraocular, intrarespiratory, or nasal inhalation and like forms of administration may be employed. Oral administration is generally preferred due to ease of administration, particularly where self-therapy is administered by the mammal.

As used herein the terms "study drug" or "study medicine" refer to either the placebo dose, the 20 mg dose of dapoxetine or the 40 mg dose of dapoxetine.

The results of an interim analysis of a randomized, double-blind, three way crossover evaluation of two prn doses of dapoxetine (20 mg and 40 mg) in the treatment of premature ejaculation (hereinafter referred to as "PE") are disclosed in tables 8a and 8b. Each patient is assigned to receive 4 to 6 administrations of each of the 3 study doses, in a random order, over 3 periods of not more than 4 weeks each. The interim analysis of the data was conducted following completion of the first treatment period.

The study comprised 155 men, aged 19 to 60, presenting with PE as defined in the DSM IV. All patients were involved in a stable monogamous sexual relationship of at least 6 months duration and reported a history of intravaginal ejaculatory latency (hereinafter referred to as "EL") of less than 2 minutes in greater than half of their intercourse experiences. History of significant cardiovascular disease or psychiatric disorder, uncontrolled hypertension, erectile dysfunction, and substance abuse were criteria for exclusion.

During a lead-in period (maximum of 4 weeks), patients were asked to record ejaculatory latency a minimum of 4 times. Latency is defined as the time span, as measured by the patient's partner via a stopwatch, from vaginal intromission to ejaculation. At the completion of the lead-in period, patients were randomized to treatment with either 20 mg or 40 mg dapoxetine or placebo. Study medication was to be ingested 1 to 3 hours prior to a planned intercourse event. The time study drug was taken and time of intercourse were recorded in an event log. Patients were instructed to attempt intercourse at least 4 times over the 4 week treatment period and were issued a sufficient supply of medication to complete 6 attempts at intercourse. The outcome of each attempt (success of intromission and EL) was recorded in the event log initialed by the patient and his partner. Patients returned to the study clinic for a follow-up visit after 4 to 6 attempts at intercourse were completed. At visits 4, 5, and 6 patients were asked to answer the Global Satisfaction Questions and to complete the PEQ.

Of the 155 patients randomized, 145 completed the treatment period. 54 patients were randomized to the placebo group, while 56 and 45 received 20 mg or 40 mg dapoxetine respectively. Although patients were randomly assigned to treatment sequences in blocks of 6, the imbalance in the number of patients randomized to each group was due to the random distribution of the 40 mg assignment to later allocations within the blocks. The intent-to-treat population was comprised of 143 patients, each of whom had baseline and follow-up data for analysis. Analysis of EL was conducted on the 138 patients who had latency data at baseline and at least one post-medication event. The percentage of patients with data sufficient for inclusion in the analysis of EL was lower in the 40 mg group than in either of the other 2 groups. This difference may be attributable to the smaller size of the 40 mg group, such that each patient represents a greater percentage of the whole, rather than being a function of the dose administered.

Patients across all three groups attempted intercourse following ingestion of study drug an average of 4.4 times. Mean ejaculatory latency at baseline (the average of all recorded EL during the 4 week lead-in period) was 18 seconds longer in the placebo group than in either dapoxetine group. An EL evaluable patient was one who had both a baseline and a follow-up latency value. It is notable that 22.5%, 16.0% and 13.5% of EL evaluable patients in the placebo, 20 mg dapoxetine and 40 mg dapoxetine groups respectively had mean baseline EL above 2 minutes, with some recording mean values as high as 7 minutes.

Tables 8a and 8b provide summaries of the ejaculatory latency in minutes for the baseline and follow-up respectively.

TABLE 8a

Baseline - 4-6 Attempts at Intercourse Lead-in

| N | Placebo 51 patients | Dapoxetine 20 mg 50 patients | Dapoxetine 40 mg 37 patients | Dapoxetine 20 & 40 mg 87 patients |
|---|---|---|---|---|
| Mean ± S.D. (minutes) | 1.6 ± 1.09 | 1.3 ± 0.91 | 1.3 ± 1.24 | 1.3 ± 1.06 |
| Range (minutes) | 0.2-5.6 | 0.1-4.2 | 0.0-7.0 | 0-7.0 |

TABLE 8b

Follow-up - 4-6 Attempts at Intercourse Treatment

| N | Placebo 51 patients | Dapoxetine 20 mg 50 patients | Dapoxetine 40 mg 37 patients | Dapoxetine 20 & 40 mg 87 patients |
|---|---|---|---|---|
| Mean ± S.D. (minutes) | 2.0 ± 1.48 | 2.3 ± 2.26 | 2.3 ± 2.19 | 2.3 ± 2.22 |
| LS Mean (minutes) | 1.74 | 2.41 | 2.52 | NA |
| Range (minutes) | 0.2-7.6 | 0.1-11.4 | 0.0-9.8 | 0.0-11.4 |
| P value v. placebo | NA | 0.0340 | 0.0228 | 0.0103 |

*NA represents "not applicable".
**LS represents "least squares", and is the mean value with adjustment for differences in baseline and sample size.

As summarized in table 8b above, the mean ejaculatory latency for all intercourse events that followed ingestion of dapoxetine increased by one minute for both the 20 mg and 40 mg dapoxetine treatment groups, while EL increased only 24 seconds in the placebo group. When the data are adjusted for sample size and baseline differences between treatments, the LS means are 1.74 minutes for placebo, 2.41 for the 20 mg dapoxetine treatment, and 2.52 for the 40 mg dapoxetine treatment. The percentage of patients achieving increases of at least one minute in EL was higher in the 20 mg (22%) and 40 mg (24%) dapoxetine groups than in the placebo group (14%).

Various modifications of the invention in addition to those shown and described herein will be apparent to those skilled in the art from the foregoing description. Such modifications are also intended to fall within the scope of the appended claims. The above disclosure includes all the information believed to be essential to enable those skilled in the art to practice the claimed invention. The cited patents or publications may provide further useful information and, thus, these cited materials are incorporated herein in their entireties by reference thereto.

The results of a final analysis of a randomized, double-blind, three way crossover evaluation of two prn doses of dapoxetine (20 mg and 40 mg) in the treatment of premature ejaculation are disclosed in the following tables. The final analyses of the data was conducted following completion of all 3 treatment periods.

TABLE 9

Ejaculatory Latency in Minutes for all Patients.

| | Placebo (LS Mean) | Dapoxetine 20 mg (LS Mean) | Dapoxetine 40 mg (LS Mean) |
|---|---|---|---|
| Ejaculatory Latency (minutes) | 2.26 | 2.78 | 3.19 |
| p-value v. placebo for ejaculatory latency | | 0.0470 | 0.0004 |
| Change in Latency (minutes) | 0.92 | 1.43 | 1.86 |
| p-value v. placebo for change in latency | | 0.0524 | 0.0004 |

TABLE 10a

Ejaculatory Latency for Patients with a Baseline of Less Than One Minute.

| | Placebo (LS Mean) | Dapoxetine 20 mg (LS Mean) | Dapoxetine 40 mg (LS Mean) |
|---|---|---|---|
| Ejaculatory Latency (minutes) | 1.1 | 1.2 | 1.7 |
| p-value v. placebo for ejaculatory latency | | | 0.009 |
| Change in Latency (minutes) | 0.5 | 0.6 | 1.3 |
| p-value v. placebo for change in latency | | | 0.008 |

TABLE 10b

Global Satisfaction for Patients with a Baseline of Less Than One Minute.

| | Placebo | Dapoxetine 20 mg | Dapoxetine 40 mg | p-value |
|---|---|---|---|---|
| Better/Much Better | 4% | 13% | 24% | <0.001 |
| ≧Slightly Better | 16% | 38% | 46% | <0.001 |

TABLE 11a

Ejaculatory Latency for Patients with a Baseline of Less Than Two Minutes.

| | Placebo (LS Mean) | Dapoxetine 20 mg (LS Mean) | Dapoxetine 40 mg (LS Mean) |
|---|---|---|---|
| Ejaculatory Latency (minutes) | 1.7 | 2.4 | 2.5 |
| p-value v. placebo for ejaculatory latency | | | 0.003 |
| Change in Latency (minutes) | 0.8 | 1.4 | 1.5 |
| p-value v. placebo for change in latency | | | 0.003 |

TABLE 11b

Global Satisfaction for Patients with a Baseline of Less Than Two Minutes.

| | Placebo | Dapoxetine 20 mg | Dapoxetine 40 mg | p-value |
|---|---|---|---|---|
| Better/Much Better | 7% | 23% | 29% | <0.001 |
| ≧Slightly Better | 28% | 50% | 50% | <0.001 |

Table 12 reveals that Dapoxetine can effectively and unexpectedly treat premature ejaculation with the first dose administered to a patient. Thus, no lead-in period is required in order to treat premature ejaculation with dapoxetine providing for effective PRN dosing.

TABLE 12

Ejaculatory Latency Recorded After Administration of a Single Dose.

| | Placebo (LS Mean) | Dapoxetine 20 mg (LS Mean) | Dapoxetine 40 mg (LS Mean) |
|---|---|---|---|
| Ejaculatory Latency (minutes) | 1.54 ± 0.24 | 2.37 ± 0.24 | 1.98 ± 0.27 |
| p-value v. placebo for ejaculatory latency | | 0.015 | 0.219 |

*p-value for dapoxetine doses combined vs. placebo = 0.038

TABLE 13a

Ejaculatory Latency for "Severe" Patients.

| | Baseline | Placebo (LS Mean) | Dapoxetine 20 mg (LS Mean) | Dapoxetine 40 mg (LS Mean) |
|---|---|---|---|---|
| Ejaculatory Latency (minutes) | 1.23 | 2.10 | 2.60 | 3.09 |
| p-value, Placebo vs 40 mg | | | | <0.0028 |
| Change in Latency (minutes) | | 0.92 | 1.42 | 1.93 |
| p-value, Placebo vs 40 mg | | | | <0.0026 |

TABLE 13b

Global Satisfaction for "Severe" Patients.

| | Placebo | Dapoxetine 20 mg | Dapoxetine 40 mg | p-value |
|---|---|---|---|---|
| Better/Much Better | 7.3% | 17.2% | 25.5% | <0.0001 |
| ≧Slightly Better | 31.0% | 48.5% | 54.1% | <0.0001 |

TABLE 14a

Ejaculatory Latency for "Moderate" Patients.

| | Baseline | Placebo (LS Mean) | Dapoxetine 20 mg (LS Mean) | Dapoxetine 40 mg (LS Mean) |
|---|---|---|---|---|
| Ejaculatory Latency (minutes) | 1.68 | 2.10 | 2.64 | 2.93 |
| p-value, Placebo vs 40 mg | | | | <0.0405 |
| Change in Latency (minutes) | | 0.45 | 0.94 | 1.27 |
| p-value, Placebo vs 40 mg | | | | <0.0516 |

TABLE 14b

Global Satisfaction for "Moderate" Patients.

| | Placebo | Dapoxetine 20 mg | Dapoxetine 40 mg | p-value |
|---|---|---|---|---|
| Better/Much Better | 13.4% | 34.4% | 50% | <0.0076 |
| ≧Slightly Better | 30.1% | 51.6% | 66.7% | <0.0076 |

TABLE 15a

Ejaculatory Latency for Patients with a Baseline ≧ Two Minutes.

| | Baseline | Placebo (LS Mean) | Dapoxetine 40 mg (LS Mean) |
|---|---|---|---|
| Ejaculatory Latency (minutes) | 3.19 | 5.24 | 6.59 |
| p-value, Placebo vs 40 mg | | | 0.18 |
| Change in Latency (minutes) | | 2.12 | 3.43 |
| p-value, Placebo vs 40 mg | | | 0.19 |

TABLE 15b

Global Satisfaction for Patients with a Baseline ≧ Two Minutes.

| | Placebo | Dapoxetine 40 mg | p-value |
|---|---|---|---|
| Better/Much Better | 13% | 39.1% | 0.09 |
| ≧Slightly Better | 43.4% | 65.2% | 0.09 |

TABLE 16a

Ejaculatory Latency for Patients with a Baseline ≧ One Minute.

| | Baseline | Placebo (LS Mean) | Dapoxetine 40 mg (LS Mean) |
|---|---|---|---|
| Ejaculatory Latency (minutes) | 1.90 | 3.16 | 4.24 |

TABLE 16a-continued

Ejaculatory Latency for Patients with a Baseline ≧ One Minute.

| | Baseline | Placebo (LS Mean) | Dapoxetine 40 mg (LS Mean) |
|---|---|---|---|
| p-value, Placebo vs 40 mg | | | 0.01 |
| Change in Latency (minutes) | | 1.32 | 2.40 |
| p-value, Placebo vs 40 mg | | | 0.01 |

TABLE 16b

Global Satisfaction for Patients with a Baseline ≧ One Minute.

| | Placebo | Dapoxetine 40 mg | p-value |
|---|---|---|---|
| Better/Much Better | 11.7% | 36.4% | <0.001 |
| ≧Slightly Better | 40.6% | 65.0% | <0.001 |

What is claimed is:

1. A method of treating or managing sexual dysfunction in a mammal in need of treatment which comprises administering on an as-needed basis to the mammal a therapeutically effective amount of dapoxetine or a pharmaceutically acceptable salt thereof, wherein the sexual dysfunction is premature ejaculation, wherein the mammal is a human male, and wherein said administration of dapoxetine is effective for treating or managing premature ejaculation in the absence of priming doses.

2. The method of claim 1, wherein dapoxetine is administered immediately prior to, to about 12 hours prior to a sexual activity.

3. The method of claim 1, wherein dapoxetine is administered immediately prior to, to about 8 hours prior to a sexual activity.

4. A method of treating or managing sexual dysfunction in a mammal in need of treatment which comprises administering on an as-needed basis to the mammal a therapeutically effective amount of dapoxetine or a pharmaceutically acceptable salt thereof, wherein the sexual dysfunction is premature ejaculation, wherein the mammal is a human male, wherein dapoxetine is administered immediately prior to, to about 4 hours prior to a sexual activity and wherein said administration of dapoxetine is effective for treating or managing premature ejaculation in the absence of priming doses.

5. The method of claim 1, wherein dapoxetine is administered immediately prior to, to about 3 hours prior to a sexual activity.

6. The method of claim 1, wherein dapoxetine is administered immediately prior to a sexual activity.

7. A method of treating premature ejaculation in a human male which comprises administering orally to the human male about 0.01 mg to about 200 mg of dapoxetine or a pharmaceutically acceptable salt thereof immediately prior to, to about 4 hours prior to a sexual activity, wherein said administration of dapoxetine is effective for treating premature ejaculation in the absence of priming doses.

8. A method of treating premature ejaculation in a human male which comprises administering orally to the human male about 0.01 mg to about 200 mg of dapoxetine or a pharmaceutically acceptable salt thereof immediately prior to, to about 3 hours prior to a sexual activity, wherein said administration of dapoxetine is effective for treating premature ejaculation in the absence of priming doses.

9. A method of treating premature ejaculation in a human male which comprises administering orally to the human male about 0.01 mg to about 200 mg of dapoxetine or a pharmaceutically acceptable salt thereof about 30 minutes to about 3 hours prior to a sexual activity, wherein said administration of dapoxetine is effective for treating premature ejaculation in the absence of priming doses.

10. A method of treating premature ejaculation in a human male which comprises administering orally to the human male about 0.01 mg to about 200 mg of dapoxetine or a pharmaceutically acceptable salt thereof immediately prior to a sexual activity, wherein said administration of dapoxetine is effective for treating premature ejaculation in the absence of priming doses.

* * * * *